(12) United States Patent
Marks et al.

(10) Patent No.: US 11,787,880 B2
(45) Date of Patent: Oct. 17, 2023

(54) HIGHLY SOLUBLE ALKYL SUBSTITUTED CARBENIUM BORATE AS CO-CATALYSTS FOR OLEFIN POLYMERIZATIONS

(71) Applicants: Dow Global Technologies LLC, Midland, MI (US); Northwestern University, Evanston, IL (US)

(72) Inventors: Tobin J. Marks, Evanston, IL (US); Yanshan Gao, Evanston, IL (US); Tracy L. Lohr, Evanston, IL (US); Matthew D. Christianson, Midland, MI (US); Jerzy Klosin, Midland, MI (US); Edmund M. Carnahan, Lake Jackson, TX (US); Andrew J. Young, Lake Jackson, TX (US)

(73) Assignees: Dow Global Technologies LLC, Midland, MI (US); Northwestern University, Evanston (IL)

( * ) Notice: Subject to any disclaimer, the term of this patent is extended or adjusted under 35 U.S.C. 154(b) by 423 days.

(21) Appl. No.: 17/043,326

(22) PCT Filed: Mar. 29, 2019

(86) PCT No.: PCT/US2019/024754
§ 371 (c)(1),
(2) Date: Sep. 29, 2020

(87) PCT Pub. No.: WO2019/191539
PCT Pub. Date: Oct. 3, 2019

(65) Prior Publication Data
US 2021/0017305 A1    Jan. 21, 2021

Related U.S. Application Data

(60) Provisional application No. 62/650,462, filed on Mar. 30, 2018.

(51) Int. Cl.
| | | |
|---|---|---|
| *C08F 10/02* | (2006.01) | |
| *C08F 2/06* | (2006.01) | |
| *C07C 15/107* | (2006.01) | |
| *C07F 5/02* | (2006.01) | |

(52) U.S. Cl.
CPC ............ *C08F 10/02* (2013.01); *C07C 15/107* (2013.01); *C07F 5/027* (2013.01); *C08F 2420/02* (2013.01)

(58) Field of Classification Search
None
See application file for complete search history.

(56) References Cited

U.S. PATENT DOCUMENTS

| | | |
|---|---|---|
| 3,773,733 A | 11/1973 | Matsushima |
| 3,860,622 A | 1/1975 | Wade |
| 4,677,088 A | 6/1987 | Huff et al. |
| 5,347,024 A | 9/1994 | Nickias et al. |
| 5,407,882 A | 4/1995 | Yamada et al. |
| 5,447,895 A | 9/1995 | Marks et al. |
| 5,536,797 A | 7/1996 | Nickias et al. |
| 5,763,549 A | 6/1998 | Elder et al. |
| 5,807,939 A | 9/1998 | Elder et al. |
| 5,895,771 A | 4/1999 | Epstein et al. |
| 5,919,983 A | 7/1999 | Rosen et al. |
| 6,153,776 A | 11/2000 | Patton et al. |
| 6,177,376 B1 | 1/2001 | Fritze et al. |
| 6,221,941 B1 | 4/2001 | Strauss et al. |
| 6,268,445 B1 | 7/2001 | McAdon et al. |
| 6,284,697 B1 | 9/2001 | Windisch et al. |
| 6,392,076 B1 | 5/2002 | Strauss et al. |
| 6,395,671 B2 | 5/2002 | LaPointe |
| 6,455,650 B1 | 9/2002 | Lipian et al. |
| 6,462,156 B2 | 10/2002 | LaPointe |

(Continued)

FOREIGN PATENT DOCUMENTS

| | | |
|---|---|---|
| CA | 2254601 A1 | 11/1998 |
| CN | 1270596 A | 10/2000 |

(Continued)

OTHER PUBLICATIONS

Arriola et al., "Catalytic Production of Olefin Block Copolymers via Chain Shuttling Polymerization", Science, 2006, 312, 714-719.
Busico, V., "Metal-catalysed olefin polymerisation into the new millennium: a perspective outlook", Dalton Transactions 2009, 8794-8802.
Delferro et al., "Multinuclear Olefin Polymerization Catalysts", Chem. Rev. 2011, 111, 2450-2485.
Ewen, J.A., "Propylene Polymerizations with Metallocene/Teal/ Trityl Tetrakis (Pentafluorophenyl) Aluminate Mixtures", Catalyst Research Corporation, Houston, Texas, pp. 405-410.
Galland et al., "13C NMR Determination of the Composition of Linear Low-Density Polyethylene Obtained with [è3-Methallyl-nickel-diimine]PF6 Complex", Macromolecules 1999, 32, 1620-1625.
Gao et al., "Highly Soluble Bis-(Alkyl Substituted Carbenium) Bis-borate as Binuclear Cocatalysts for Olefin Polymerizations", Department of Chemistry, Northwestern University, pp. 1-4.

(Continued)

*Primary Examiner* — Fred M Teskin
(74) *Attorney, Agent, or Firm* — Dinsmore & Shohl LLP

(57) ABSTRACT

Embodiments are directed to catalyst systems comprising: a procatalyst; and a co-catalyst, the co-catalyst comprising: a non-coordinating borate anion having the formula $[B(C_6F_5)_4]^{1-}$ and a cation according to formula (I).

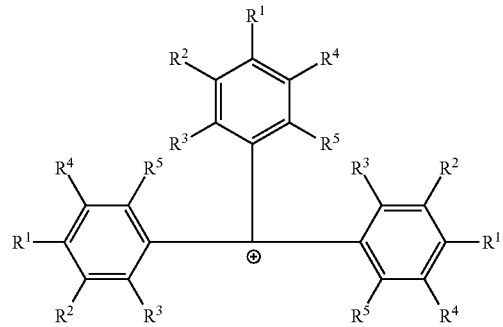

(I)

15 Claims, No Drawings

(56) References Cited

U.S. PATENT DOCUMENTS

| | | |
|---|---|---|
| 6,627,573 B2 | 9/2003 | Babb et al. |
| 6,777,509 B2 | 8/2004 | Brown et al. |
| 6,869,904 B2 | 3/2005 | Boussie et al. |
| 6,900,321 B2 | 5/2005 | Boussie et al. |
| 6,953,764 B2 | 10/2005 | Frazier et al. |
| 7,078,546 B2 | 7/2006 | Piers et al. |
| 7,511,104 B2 | 3/2009 | Pehlert et al. |
| 7,579,416 B2 | 8/2009 | Mihan |
| 7,619,047 B2 | 11/2009 | Yang et al. |
| 7,650,930 B2 | 1/2010 | Cheluget et al. |
| 7,683,194 B2 | 3/2010 | Krossing et al. |
| 8,372,927 B2 | 2/2013 | Figueroa et al. |
| 9,243,090 B2 | 1/2016 | Arriola et al. |
| 9,349,895 B2 | 5/2016 | Ikenaga et al. |
| 9,362,436 B2 | 6/2016 | Nanjundiah et al. |
| 10,457,765 B2 * | 10/2019 | Qin .......................... C07F 7/10 |
| 2004/0162215 A1 | 8/2004 | Vogel |
| 2007/0149386 A1 | 6/2007 | Mihan |
| 2008/0033125 A1 | 2/2008 | Solan et al. |
| 2008/0249264 A1 | 10/2008 | Hanefeld et al. |
| 2008/0275189 A1 | 11/2008 | Carnahan et al. |
| 2008/0311812 A1 | 12/2008 | Arriola et al. |
| 2009/0209713 A1 | 8/2009 | McGuiness et al. |
| 2009/0270571 A1 | 10/2009 | Wang et al. |
| 2010/0048842 A1 | 2/2010 | Figueroa et al. |
| 2015/0094433 A1 | 4/2015 | Hoang et al. |
| 2015/0094434 A1 | 4/2015 | Tohi et al. |
| 2015/0099856 A1 | 4/2015 | Hoang et al. |
| 2019/0040086 A1 | 2/2019 | Holub et al. |
| 2021/0054119 A1 | 2/2021 | Senecal et al. |

FOREIGN PATENT DOCUMENTS

| | | |
|---|---|---|
| CN | 102451758 A | 5/2012 |
| EP | 707014 A1 | 4/1996 |
| EP | 824112 A1 | 2/1998 |
| EP | 856523 A1 | 8/1998 |
| EP | 573403 B1 | 11/1998 |
| EP | 1056752 A1 | 12/2000 |
| EP | 1074555 A2 | 2/2001 |
| EP | 1308449 A2 | 5/2003 |
| EP | 2221328 A2 | 8/2010 |
| EP | 2468758 A2 | 6/2012 |
| FR | 2942230 A1 | 8/2010 |
| JP | H05-155927 A | 6/1993 |
| JP | 11286491 A | 10/1999 |
| JP | 20110231292 A | 11/2011 |
| WO | 9735893 A1 | 10/1997 |
| WO | 9849212 A1 | 11/1998 |
| WO | 9906413 A1 | 2/1999 |
| WO | 19910005534 A1 | 4/1999 |
| WO | 9941294 A1 | 8/1999 |
| WO | 0053611 A1 | 9/2000 |
| WO | 0063262 A2 | 10/2000 |
| WO | 0123442 A1 | 4/2001 |
| WO | 0130785 A1 | 5/2001 |
| WO | 0158969 A1 | 8/2001 |
| WO | 03101936 A1 | 12/2003 |
| WO | 2005054254 A1 | 6/2005 |
| WO | 2005063829 A1 | 7/2005 |
| WO | 2007136494 A2 | 11/2007 |
| WO | 2007136496 A2 | 11/2007 |
| WO | 2008038173 A2 | 4/2008 |
| WO | 2010022228 A2 | 2/2010 |
| WO | 2010139684 A1 | 12/2010 |
| WO | 2011102989 A1 | 8/2011 |
| WO | 2014209927 A1 | 12/2014 |
| WO | 2017173080 A1 | 10/2017 |

OTHER PUBLICATIONS

Gao et al., "Supporting Information for Highly Soluble Bis-(Alkyl Substituted Carbenium) Bis-borate as Binuclear Cocatalysts for Olefin Polymerizations", Department of Chemistry, Northwestern University, S1-S26.

International Search Report and Written Opinion pertaining to PCT/US2019/023643, dated Jul. 3, 2019.

International Search Report and Written Opinion pertaining to PCT/US2019/024034, dated Jun. 26, 2019.

International Search Report and Written Opinion pertaining to PCT/US2019/024075, dated Jun. 26, 2019.

International Search Report and Written Opinion pertaining to PCT/US2019/024599, dated Jul. 10, 2019.

International Search Report and Written Opinion pertaining to PCT/US2019/024754, dated Jul. 30, 2019.

Jung et al., "Analysis of Chain Branch of Polyolefins by a New Proton NMR Approach", Anal. Chem. 2016, 88, 1516-1520.

Klosin et al., "Development of Group IV Molecular Catalysts for High Temperature Ethylene-α-Olefin Copolymerization Reactions", Acc. Chem. Res. 2015, 48, 2004-2016.

Kraft et al., "Synthesis and Application of Strong Bransted Acids Generated from the Lewis Acid Al(ORF)3 and an Alcohol", Organometallics 2012, 31 (21), 7485-7491.

Krossing, I., "The Facile Preparation of Weakly Coordinating Anions: Structure and Characterisation of Silverpolyfluoroalkoxyaluminates AgAl(ORF)4, Calculation of the Alkoxide Ion Affinity", Chem. Eur. J. 2001, 7, 490.

Krossing, I., "Chemistry with Weakly-Coordinating Fluorinated Alkoxyaluminate Anions: Gas Phase Cations in Condensed Phases?", Coord. Chem. Rev., 2006, 250, 2721-2744.

Lapointe et al., "New Family of Weakly Coordinating Anions", J. Am. Chem. Soc., 2000, 122, 9560-9561.

Li et al., "Coordination Copolymerization of Severely Encumbered Isoalkenes with Ethylene: Enhanced Enchainment Mediated by Binuclear Catalysts and Cocatalysts", J. Am. Chem. Soc. 2005, 127, 14756-14768.

Li et al., "Nuclearity and cooperativity effects in binuclear catalysts and cocatalysts for olefin polymerization", Proc. Natl. Acad. Sci. U. S. A. 2006, 103, 15295-15302.

Li et al., "Catalyst/Cocatalyst Nuclearity Effects in Single-Site Polymerization. Enhanced Polyethylene Branching and r-Olefin Comonomer Enchainment in Polymerizations Mediated by Binuclear Catalysts and Cocatalysts via a New Enchainment Pathway", J. Am. Chem. Soc. 2002, 124, 12725-12741.

Makio et al., "FI Catalysts for Olefin Polymerization—A Comprehensive Treatment", Chem. Rev. 2011, 111, 2363-2449.

McGuinness et al., "Cocatalyst Influence in Selective Oligomerization: Effect on Activity, Catalyst Stability, and 1-Hexene/1-Octene Selectivity in the Ethylene Trimerization and Tetramerization Reaction", Organometallics 2007, 26 (10), 2561-2569.

McInnis et al., "Multinuclear Group 4 Catalysis: Olefin Polymerization Pathways Modified by Strong Metal-Metal Cooperative Effects", Acc. Chem. Res. 2014, 47, 2545-2557.

Pangborn et al., "Safe and Convenient Procedure for Solvent Purification", Organometallics 1996, 15 (5), 1518-1520.

Nakazawa et al., "A Synthetic Two-Spin Quantum Bit: g-Engineered Exchange-Coupled Biradical Designed for Controlled-NOT Gate Operations", Angew. Chem., Int. Ed. 2012, 51, 9860-9864.

Strauss et al., "Relative Lewis Basicities of Six Al(ORF)4ÿ Superweak Anions and the Structures of LiAl{OCH(CF3) 2}4 and [1-Et-3-Me-1,3-C3H3N2]-[Li{Al{OCH(CF3)2}4}2]", Chem. Eur. J. 2001, 7, 503.

Strauss et al., "LiAl(OC(Ph)(CF3)2)4: A Hydrocarbon-Soluble Catalyst for Carbon-Carbon Bond-Forming Reactions", Organometallics 1996, 15, 3776.

Sturzel et al., "From Multisite Polymerization Catalysis to Sustainable Materials and All-Polyolefin Composites", Chem. Rev. 2016, 116, 1398-1433.

Sun et al., "Al-, Nb- and Ta-based Perfluoroaryloxide Anions as Cocatalysts for Metallocene-Mediated Ziegler-Natta Olefin Polymerization", Organometallics, 2000, 1625-1627.

Yano et al., "Influence of activators on ethylene polymerization with—diphenylmethylidene-cyclopentadienyl/-fluorenyl/zirconium dichloride catalysts at high temperature", J. Mol. Catal. A: Chem. 1999, 148, 77.

(56) References Cited

OTHER PUBLICATIONS

European Office Communication pursuant to Article 94(3) EPC dated Jul. 13, 2022 for European Patent Application No. 19716692.9, 5 pgs.

U.S. Notice of Allowance and Fee(s) Due dated Apr. 26, 2022 pertaining to U.S. Appl. No. 17/043,304, filed Sep. 29, 2020, pp. 1-13.

Krossing, Ingo et al. "New reagents to introduce weakly coordinating anions of type Al(ORF)4-: synthesis, structure and characterization of Cs and trityl salts" Journal of Fluorine Chemistry, 2001, pp. 83-90, 112, Elsevier Science B.V.

Metz, Matthew V. et al. "Weakly Coordinating Al-, Nb-, Ta-, Y-, and La-Based Perfluoroaryloxymetalate Anions as Cocatalyst Components for Single-Site Olefin Polymerization" Organometallics, 2002, pp. 3691-3702, 21.

U.S. Office Action dated Aug. 11, 2021 pertaining to U.S. Appl. No. 17/043,304, filed Sep. 29, 2020, 29 pages.

International Search Report and Written Opinion dated Sep. 13, 2021 pertaining to Int'l Patent Application No. PCT/US2021/031233, 32 pgs.

Non-Final Office Action dated Jan. 14, 2022, pertaining to U.S. Appl. No. 17/043,483 22 pages.

Examination Report dated Nov. 11, 2022, pertaining to EP Patent Application No. 19716696.0, 6 pgs.

Translation of Chinese Office Action and Search Report dated Sep. 30, 2022, pertaining to CN Patent Application No. 201980022075.0, 7 pgs.

Chinese Office Action, dated Sep. 21, 2022, pertaining to Chinese Patent Application No. 201980021980.4, 2 pages.

Chinese Search Report, dated Sep. 21, 2022, pertaining to Chinese Patent Application No. 201980021980.4, 3 pages.

Chinese Office Action, dated Sep. 21, 2022, pertaining to Chinese Patent Application No. 201980021695.2, 7 pages.

Chinese Search Report, dated Sep. 21, 2022, pertaining to Chinese Patent Application No. 201980021695.2, 4 pages.

International Search Report and Written Opinion dated Sep. 13, 2021 pertaining to International application No. PCT/US2021/031233 filed May 7, 2021, 11 pages.

U.S. Office Action dated Jun. 12, 2023, pertaining to U.S. Appl. No. 17/043,029, 61 pgs.

Japanese Office Action dated Mar. 28, 2023, pertaining to JP Patent Application No. 2020-551554, 42 pgs.

\* cited by examiner

HIGHLY SOLUBLE ALKYL SUBSTITUTED CARBENIUM BORATE AS CO-CATALYSTS FOR OLEFIN POLYMERIZATIONS

CROSS-REFERENCE TO RELATED APPLICATIONS

This application is a National Stage Entry under 35 U.S.C. § 371 of International Patent Application No. PCT/US2019/024754, filed Mar. 29, 2019, which claims the benefit of U.S. Provisional Patent Application Ser. No. 62/650,462 filed Mar. 30, 2018, both of which are hereby incorporated by reference in their entireties.

TECHNICAL FIELD

Embodiments of the present disclosure generally relate to highly soluble borate anionic co-catalysts.

BACKGROUND

Since the discovery by Ziegler and Natta of heterogeneous olefin polymerizations, global polyolefin production reached approximately 150 million tons per year in 2015, and it is rising due to increasing market demand. This success is based in part on a series of important breakthroughs in co-catalyst technology. The co-catalysts discovered include aluminoxanes, boranes, and borates with triphenylcarbenium or ammonium cations. These co-catalysts activate homogeneous single-site olefin polymerization procatalysts, and polyolefins have been produced using these co-catalysts in industry.

Borate based co-catalysts in particular have contributed significantly to the fundamental understanding of olefin polymerization mechanisms and have enhanced the ability for precise control over polyolefin microstructures by deliberately tuning catalyst structures and processes. This result has stimulated interest in mechanistic studies and led to the development of novel homogeneous olefin polymerization catalyst systems that have precise control over polyolefin microstructures and performance.

SUMMARY

Despite the unique properties of the molecular catalyst systems that combine borate co-catalysts and Ziegler-Natta procatalysts, the molecular catalyst systems are not easily solubilized in apolar solvents, such as toluene or methylcyclohexane. Since ethylene and other olefins are often commercially polymerized in apolar solvents, a large amount of solvent or a halogenated solvent, such as difluorobenzene, dichlorobenzene, dichloromethane, and chloroform, is used to dissolve the components of the catalyst system. However, trace amounts of halogenated solvents may interact adversely with the co-catalysts, and a small amount of halogenated solvent may greatly decrease the activity of the catalyst system, which may affect the polymer yield and other polymer properties. Additionally, if the procatalyst or co-catalyst is insoluble or only slightly soluble in the solvent, the activity of the catalyst system may be greatly decreased as well. As a result, there is an ongoing need to solubilize catalyst systems in small amounts of solvent, especially in apolar solvents, while maintaining catalyst efficiency, reactivity, and the ability to produce polymers with good physical properties.

According to some embodiments, a catalyst system may include a procatalyst; and a co-catalyst that includes a non-coordinating borate anion having the formula $[B(C_6F_5)_4]^{1-}$ and a cation according to formula (I):

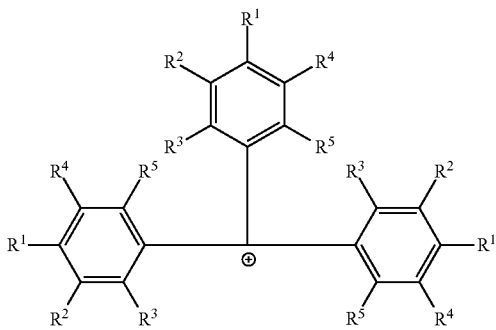

In formula (I), each $R^1$, $R^2$, $R^3$, $R^4$, and $R^5$ is independently chosen from —H, —F, —Cl, substituted or unsubstituted $(C_4-C_{40})$alkyl, substituted, or unsubstituted $(C_4-C_{40})$alkenyl or substituted or unsubstituted $(C_4-C_0)$cycloalkyl. The substituted $(C_4-C_{40})$alkyl and substituted $(C_4-C_{40})$cycloalkyl are substituted with one or more $R^S$, where each $R^S$ is chosen from $(C_1-C_{20})$alkyl or halogen. The co-catalyst may be dissolved in a non-halogenated hydrocarbon solvent.

DETAILED DESCRIPTION

Specific embodiments of catalyst systems will now be described. It should be understood that the catalyst systems of this disclosure may be embodied in different forms and should not be construed as limited to the specific embodiments set forth in this disclosure. Rather, embodiments are provided so that this disclosure will be thorough and complete, and will fully convey the scope of the subject matter to those skilled in the art.

Common abbreviations are listed below:

Me: methyl; Et: ethyl; Ph: phenyl; Bn: benzyl; i-Pr: iso-propyl; t-Bu: tert-butyl; t-Oct: tert-octyl (2,4,4-trimethylpentan-2-yl); Tf: trifluoromethane sulfonate; THF: tetrahydrofuran; $Et_2O$: diethyl ether; $CH_2Cl_2$: dichloromethane; CV: column volume (used in column chromatography); EtOAc: ethyl acetate; $C_6D_6$: deuterated benzene or benzene-d6; $CDCl_3$: deuterated chloroform; $Na_2SO_4$: sodium sulfate; $MgSO_4$: magnesium sulfate; HCl: hydrogen chloride; n-BuLi: butyllithium; t-BuLi: tert-butyllithium; MAO: methylaluminoxane; MMAO: modified methylaluminoxane; GC: gas chromatography; LC: liquid chromatography; NMR: nuclear magnetic resonance; MS: mass spectrometry; mmol: millimoles; mL: milliliters; M: molar; min or mins: minutes; h or hrs: hours; d: days.

The term "independently selected" is used herein to indicate that the R groups, such as, $R^1$, $R^2$, $R^3$, $R^4$, and $R^5$, can be identical or different (e.g., $R^1$, $R^2$, $R^3$, $R^4$, and $R^5$ may all be substituted alkyls or $R^1$ and $R^2$ may be a substituted alkyl and $R^3$ may be an aryl, etc.). A chemical name associated with an R group is intended to convey the chemical structure that is recognized in the art as corresponding to that of the chemical name. Thus, chemical names are intended to supplement and illustrate, not preclude, the structural definitions known to those of skill in the art.

The term "procatalyst" refers to a transition metal compound that has olefin polymerization catalytic activity when combined with an activator. The term "activator" refers to a compound that chemically reacts with a procatalyst in a manner that converts the procatalyst to a catalytically active catalyst. As used herein, the terms "co-catalyst" and "activator" are interchangeable terms.

When used to describe certain carbon atom-containing chemical groups, a parenthetical expression having the form "($C_x$-$C_y$)" means that the unsubstituted form of the chemical group has from x carbon atoms to y carbon atoms, inclusive of x and y. For example, a ($C_1$-$C_{50}$)alkyl is an alkyl group having from 1 to 50 carbon atoms in its unsubstituted form. In some embodiments and general structures, certain chemical groups may be substituted by one or more substituents such as $R^S$. An $R^S$ substituted chemical group defined using the "($C_x$-$C_y$)" parenthetical may contain more than y carbon atoms depending on the identity of any groups $R^S$. For example, a "($C_1$-$C_{50}$)alkyl substituted with exactly one group $R^S$, where $R^S$ is phenyl (—$C_6H_5$)" may contain from 7 to 56 carbon atoms. Thus, in general when a chemical group defined using the "($C_x$-$C_y$)" parenthetical is substituted by one or more carbon atom-containing substituents $R^S$, the minimum and maximum total number of carbon atoms of the chemical group is determined by adding to both x and y the combined sum of the number of carbon atoms from all of the carbon atom-containing substituents $R^S$.

The term "substitution" means that at least one hydrogen atom (—H) bonded to a carbon atom of a corresponding unsubstituted compound or functional group is replaced by a substituent (e.g. $R^S$). The term "—H" means a hydrogen or hydrogen radical that is covalently bonded to another atom. "Hydrogen" and "—H" are interchangeable, and unless clearly specified have identical meanings.

The term "($C_1$-$C_{50}$)alkyl" means a saturated straight or branched hydrocarbon radical containing from 1 to 50 carbon atoms; and the term "($C_1$-$C_{30}$)alkyl" means a saturated straight or branched hydrocarbon radical of from 1 to 30 carbon atoms. Each ($C_1$-$C_{50}$)alkyl and ($C_1$-$C_{30}$)alkyl may be unsubstituted or substituted by one or more $R^S$. In some examples, each hydrogen atom in a hydrocarbon radical may be substituted with $R^S$, such as, for example trifluoromethyl. Examples of unsubstituted ($C_1$-$C_{50}$)alkyl are unsubstituted ($C_1$-$C_{20}$)alkyl; unsubstituted ($C_1$-$C_{10}$)alkyl; unsubstituted ($C_1$-$C_5$)alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{40}$)alkyl are substituted ($C_1$-$C_{20}$)alkyl, substituted ($C_1$-$C_{10}$)alkyl, trifluoromethyl, and [$C_{45}$]alkyl. The term "[$C_{45}$]alkyl" means there is a maximum of 45 carbon atoms in the radical, including substituents, and is, for example, a ($C_{27}$-$C_{40}$)alkyl substituted by one $R^S$, which is a ($C_1$-$C_5$)alkyl, such as, for example, methyl, trifluoromethyl, ethyl, 1-propyl, 1-methylethyl, or 1,1-dimethylethyl. More broadly, the term "[$C_z$]alkyl" means there is a maximum of z carbon atoms, wherein z is a positive integer, in the radical, including substituents.

The term ($C_3$-$C_{50}$)alkenyl means a branched or unbranched, cyclic or acyclic monovalent hydrocarbon radical containing from 3 to 50 carbon atoms, at least one double bond and is unsubstituted or substituted by one or more $R^S$. Examples of unsubstituted ($C_3$-$C_{50}$)alkenyl: n-propenyl, isopropenyl, n-butenyl, isobutenyl, octenyl, decenyl, cyclopentenyl, cyclopentadienyl, cyclohexenyl, and cyclohexadienyl. Examples of substituted ($C_3$-$C_{50}$)alkenyl: (2-trifluoromethyl)pent-1-enyl, (3-methyl)hex-1-eneyl, (3-methyl)hexa-1,4-dienyl and (Z)-1-(6-methylhept-3-en-1-yl)cyclohex-1-eneyl.

The term "($C_3$-$C_{50}$)cycloalkyl" means a saturated cyclic hydrocarbon radical of from 3 to 50 carbon atoms that is unsubstituted or substituted by one or more $R^S$. Other cycloalkyl groups (e.g., ($C_x$-$C_y$)cycloalkyl) are defined in an analogous manner as having from x to y carbon atoms and being either unsubstituted or substituted with one or more $R^S$. Examples of unsubstituted ($C_3$-$C_{40}$)cycloalkyl are unsubstituted ($C_3$-$C_{20}$)cycloalkyl, unsubstituted ($C_3$-$C_{10}$)cycloalkyl, cyclopropyl, cyclobutyl, cyclopentyl, cyclohexyl, cycloheptyl, cyclooctyl, cyclononyl, and cyclodecyl. Examples of substituted ($C_3$-$C_{40}$)cycloalkyl are substituted ($C_3$-$C_{20}$)cycloalkyl, substituted ($C_3$-$C_{10}$)cycloalkyl, and 1-fluorocyclohexyl.

The term "halogen atom" or "halogen" means the radical of a fluorine atom (F), chlorine atom (Cl), bromine atom (Br), or iodine atom (I). The term "halide" means anionic form of the halogen atom, i.e., fluoride (F⁻), chloride (Cl⁻), bromide (Br⁻), or iodide (F⁻).

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents $R^S$, one or more double or triple bonds optionally may be present in substituents $R^S$. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents $R^S$, if any, or in aromatic rings or heteroaromatic rings, if any.

Embodiments of this disclosure include catalyst systems that include a procatalyst; and a co-catalyst comprising: a non-coordinating borate anion having the formula [$B(C_6F_5)_4$]$^{1-}$ and a cation according to formula (I):

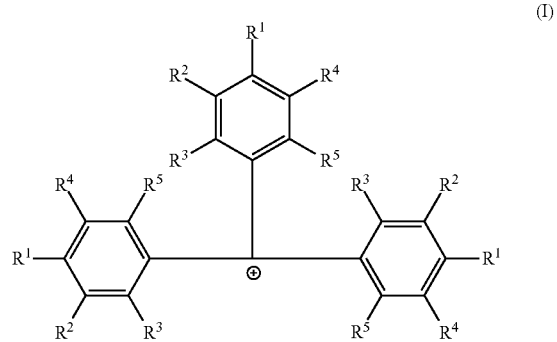

(I)

In formula (I) each $R^1$, $R^2$, $R^3$, $R^4$, and $R^5$ is independently chosen from —H, —F, —Cl, substituted or unsubstituted ($C_4$-$C_{40}$)alkyl, substituted or unsubstituted ($C_4$-$C_{40}$)alkenyl or substituted or unsubstituted ($C_4$-$C_{40}$)cycloalkyl. The substituted ($C_4$-$C_{40}$)alkyl and substituted ($C_4$-$C_{40}$)cycloalkyl are substituted with one or more $R^S$, where each $R^S$ is chosen from ($C_1$-$C_{20}$)alkyl or halogen. Furthermore, at least one of $R^1$, $R^2$, $R^3$, $R^4$, and $R^5$ is substituted or unsubstituted ($C_4$-$C_{40}$)alkyl or substituted or unsubstituted ($C_4$-$C_{40}$)cycloalkyl. The cocatalyst may be dissolved in a non-halogenated hydrocarbon solvent.

In some embodiments of formula (I), each $R^1$, $R^2$, $R^3$, $R^4$, and $R^5$ is independently chosen from —H or ($C_4$-$C_{40}$)alkyl. Furthermore, each $R^1$ is independently ($C_4$-$C_{40}$)alkyl or ($C_4$-$C_{40}$)cycloalkyl, each $R^2$ is independently ($C_4$-$C_{40}$)alkyl or ($C_4$-$C_{40}$)cycloalkyl, each $R^3$ is independently ($C_4$-$C_{40}$)alkyl or ($C_4$-$C_{40}$)cycloalkyl, each $R^4$ is independently ($C_4$-$C_{40}$)alkyl or ($C_4$-$C_{40}$)cycloalkyl, or each $R^5$ is independently ($C_4$-$C_{40}$)alkyl or ($C_4$-$C_{40}$)cycloalkyl.

In one or more embodiments, each $R^1$ is independently ($C_4$-$C_{40}$)alkyl. In some embodiments, each $R^4$ is ($C_4$-$C_{40}$)alkyl or each $R^2$ is ($C_4$-$C_{40}$)alkyl. In other embodiments, each $R^1$ is independently ($C_4$-$C_{40}$)alkyl or ($C_4$-$C_{40}$)cycloalkyl, and each $R^4$ is ($C_4$-$C_{40}$)alkyl or each $R^2$ is ($C_4$-$C_{40}$)alkyl.

In one or more embodiments, each $R^1$, $R^2$, $R^3$, $R^4$, or $R^5$ is optionally substituted [$C_{50}$]alkyl. The substituted [$C_{50}$]

alkyl is substituted with one or more $R^S$, where each $R^S$ is chosen from $(C_1-C_{20})$alkyl or halogen.

In one or more embodiments, each $R^1$ is independently chosen from unsubstituted $(C_5-C_{20})$alkyl, unsubstituted $(C_6-C_{20})$alkyl, unsubstituted $(C_5-C_8)$alkyl, unsubstituted $(C_8-C_{30})$alkyl, or tallow alkyl. In some embodiments, each $R^1$ is independently chosen from 1,1-dimethylethyl (also called tert-butyl), n-butyl, 1-pentyl, 1-hexyl, heptyl, n-octyl, tert-octyl, nonyl, decyl, undecyl, or dodecyl. In other embodiments, $R^1$ is independently chosen from a linear $(C_4-C_{30})$alkyl, a linear $(C_5-C_{30})$alkyl, or branched $(C_5-C_{30})$alkyl. In some embodiments, each $R^1$ is independently chosen from saturated $[C_3]$alkyl.

In one or more embodiments, each $R^2$, $R^3$, $R^4$ and $R^5$ is —H.

In one or more embodiments, the co-catalyst has a solubility of greater than 20 milligrams per milliliter (mg/mL) in toluene at standard temperature and pressure (STP) (temperature of 22.5±2.5° C. and a pressure of approximately 1 atmosphere). In some embodiments, the co-catalyst has a solubility of from 20 to 100 mg/mL in toluene under STP. In other embodiments, the co-catalyst has a solubility of from 25 to 100 mg/mL in toluene under STP. All subranges in the range of from 20 to 100 mg/mL are included herein. All individual values and subranges from at least 20 to 100 mg/mL in toluene are included herein and disclosed herein as separate embodiments. For example, any one of the co-catalyst according to this disclosure may include at least 21 mg/mL; at least 25 mg/mL, or at least 30 mg/mL in toluene.

In one or more embodiments, the co-catalyst has a solubility of greater than 20 milligrams per milliliter (mg/mL) in methylcyclohexane (MCH) at standard temperature and pressure (STP) (temperature of 22.5±2.5° C. and a pressure of approximately 1 atmosphere). In some embodiments, the co-catalyst has a solubility of from 20 to 100 mg/mL in MCH under STP. All individual values and subranges from at least 20 to 100 mg/mL in MCH are included herein and disclosed herein as separate embodiments. For example, any one of the co-catalyst according to this disclosure may include at least 21 mg/mL; at least 25 mg/mL, or at least 30 mg/mL in MCH.

Solubility of a compound is determined at least in part by entropic effects in the solvent system. The entropic effects may include, for example, changes in lattice energy, solvation, solvent structure, or combinations thereof. Solvation is related to the interactions between a solute (such as an activator or co-catalyst) and molecules of the solvent. Without intending to be bound by theory, it is believed that increasing the number of carbon atoms in any one of each one of $R^1$, $R^2$, $R^3$, $R^4$, and $R^5$ may, in turn, increase the solubility of the co-catalyst as a result of increase solvation. Additionally, it is believed that linear alkyl groups may render the co-catalyst more soluble in non-polar solvents than a branched alkyl groups in the same solvent, because the linear alkyl has a greater surface area than the branched alkyl. The increased surface area increases the solvent-solute interaction (i.e., solvation increases), thereby increasing the solubility of the linear alkyl in non-polar solvents, compared to the solubility of the branched alkyl in the same solvents.

Generally, a solute may have similar solubilities in different non-polar solvents. Non-polar solvents generally include hydrocarbon solvents. A non-limiting list of non-polar hydrocarbon solvents include: hexanes, cyclohexane, methylcyclohexane, heptanes, kerosene, toluene, xylenes, turpentine, and ISOPAR-E™ and combinations thereof. In the Example section, the co-catalysts, as described in this disclosure, sufficiently process polymers in a solvent system that includes methylcyclohexane or ISOPAR-E™, both of which are non-polar solvents, and more specifically are hydrocarbon solvents. Therefore, it is believed that the co-catalysts of this disclosure may sufficiently process polymers in other solvent systems.

In one or more embodiments, the catalyst system includes a catalyst, in which the catalyst is ionic. Not intending to be limiting, examples of the homogeneous catalysts include metallocene complexes, constrained geometry metal-ligand complexes (Li, H.; Marks, T. J., *Proc. Natl. Acad. Sci. U.S.A* 2006, 103, 15295-15302; Li, H.; Li, L.; Schwartz, D. J.; Metz, M. V.; Marks, T. J.; Liable-Sands, L.; Rheingold, A. L., *J. Am. Chem. Soc.* 2005, 127, 14756-14768; McInnis, J. P.; Delferro, M.; Marks, T. J., *Acc. Chem. Res.* 2014, 47, 2545-2557; Delferro, M.; Marks, T. J., *Chem. Rev.* 2011, 111, 2450-2485.), pyridylamido Hf (or Zr, Ti) complexes (Arriola, D. J.; Carnahan, E. M.; Hustad, P. D.; Kuhlman, R. L.; Wenzel, T. T., *Science,* 2006, 312, 714-719.; Arriola, D. J.; Carnahan, E. M.; Cheung, Y. W.; Devore, D. D.; Graf, D. D.; Hustad, P. D.; Kuhlman, R. L.; Shan, C. L. P.; Poon, B. C.; Roof, G. R., U.S. Pat. No. 9,243,090 B2, 2016.), phenoxyimine metal complexes (Makio, H.; Terao, H.; Iwashita, A.; Fujita, T., *Chem. Rev.* 2011, 111, 2363-2449.), bis-biphenylphenoxy metal-ligand complexes (Arriola, D. J.; Bailey, B. C.; Klosin, J.; Lysenko, Z.; Roof, G. R.; Smith, A. J. WO2014209927A1, 2014.), etc. The following references summarize metal complexes as olefin polymerization catalysts both in industry and academia: Stürzel, M.; Mihan, S.; Mülhaupt, R., *Chem. Rev.* 2016, 116, 1398-1433.; Busico, V., *Dalton Transactions* 2009, 8794-8802.; Klosin, J.; Fontaine, P. P.; Figueroa, R., *Acc. Chem. Res.* 2015, 48, 2004-2016.

Polyolefins

The catalytic systems described in the preceding paragraphs are utilized in the polymerization of olefins, primarily ethylene and propylene, to form ethylene-based polymers or propylene-based polymers. In some embodiments, there is only a single type of olefin or α-olefin in the polymerization scheme, creating a homopolymer. However, additional α-olefins may be incorporated in the polymerization procedure. The additional α-olefin co-monomers typically have no more than 20 carbon atoms. For example, the α-olefin co-monomers may have 3 to 10 carbon atoms or 3 to 8 carbon atoms. Exemplary α-olefin co-monomers include, but are not limited to, propylene, 1-butene, 1-pentene, 1-hexene, 1-heptene, 1-octene, 1-nonene, 1-decene, and 4-methyl-1-pentene. For example, the one or more α-olefin co-monomers may be selected from the group consisting of propylene, 1-butene, 1-hexene, and 1-octene; or in the alternative, from the group consisting of 1-hexene and 1-octene.

The ethylene-based polymers, for example homopolymers and/or interpolymers (including copolymers) of ethylene and optionally one or more co-monomers such as α-olefins, may comprise from at least 50 mole percent (mol %) monomer units derived from ethylene. All individual values and subranges encompassed by "from at least 50 mole percent" are disclosed herein as separate embodiments; for example, the ethylene-based polymers, homopolymers and/or interpolymers (including copolymers) of ethylene and optionally one or more co-monomers such as α-olefins may comprise at least 60 mole percent monomer units derived from ethylene; at least 70 mole percent monomer units derived from ethylene; at least 80 mole percent monomer units derived from ethylene; or from 50 to 100 mole percent monomer units derived from ethylene; or from 80 to 100 mole percent monomer units derived from ethylene.

In some embodiments, the ethylene-based polymers may comprise at least 90 mole percent units derived from ethylene. All individual values and subranges from at least 90 mole percent are included herein and disclosed herein as separate embodiments. For example, the ethylene-based polymers may comprise at least 93 mole percent units derived from ethylene; at least 96 mole percent units; at least 97 mole percent units derived from ethylene; or in the alternative, from 90 to 100 mole percent units derived from ethylene; from 90 to 99.5 mole percent units derived from ethylene; or from 97 to 99.5 mole percent units derived from ethylene.

In some embodiments of the ethylene-based polymer, the amount of additional α-olefin is less than 50 mol %; other embodiments include at least 1 mole percent (mol %) to 25 mol %; and in further embodiments the amount of additional α-olefin includes at least 5 mol % to 103 mol %. In some embodiments, the additional α-olefin is 1-octene.

Any conventional polymerization processes may be employed to produce the ethylene-based polymers. Such conventional polymerization processes include, but are not limited to, solution polymerization processes, gas phase polymerization processes, slurry phase polymerization processes, and combinations thereof using one or more conventional reactors such as loop reactors, isothermal reactors, fluidized bed gas phase reactors, stirred tank reactors, batch reactors in parallel, series, or any combinations thereof, for example.

In one embodiment, the ethylene-based polymer may be produced via solution polymerization in a dual reactor system, for example a dual loop reactor system, wherein ethylene and optionally one or more α-olefins are polymerized in the presence of the catalyst system, as described herein, and optionally one or more co-catalysts. In another embodiment, the ethylene-based polymer may be produced via solution polymerization in a dual reactor system, for example a dual loop reactor system, wherein ethylene and optionally one or more α-olefins are polymerized in the presence of the catalyst system in this disclosure, and as described herein, and optionally one or more other catalysts. The catalyst system, as described herein, can be used in the first reactor, or second reactor, optionally in combination with one or more other catalysts. In one embodiment, the ethylene-based polymer may be produced via solution polymerization in a dual reactor system, for example a dual loop reactor system, wherein ethylene and optionally one or more α-olefins are polymerized in the presence of the catalyst system, as described herein, in both reactors.

In another embodiment, the ethylene-based polymer may be produced via solution polymerization in a single reactor system, for example a single loop reactor system, in which ethylene and optionally one or more α-olefins are polymerized in the presence of the catalyst system, as described within this disclosure, and optionally one or more co-catalysts, as described in the preceding paragraphs.

The ethylene-based polymers may further comprise one or more additives. Such additives include, but are not limited to, antistatic agents, color enhancers, dyes, lubricants, pigments, primary antioxidants, secondary antioxidants, processing aids, UV stabilizers, and combinations thereof. The ethylene-based polymers may contain any amounts of additives. The ethylene-based polymers may compromise from about 0 to about 10 percent by the combined weight of such additives, based on the weight of the ethylene-based polymers and the one or more additives. The ethylene-based polymers may further comprise fillers, which may include, but are not limited to, organic or inorganic fillers. The ethylene-based polymers may contain from about 0 to about 20 weight percent fillers such as, for example, calcium carbonate, talc, or $Mg(OH)_2$, based on the combined weight of the ethylene-based polymers and all additives or fillers. The ethylene-based polymers may further be blended with one or more polymers to form a blend.

In some embodiments, a polymerization process for producing an ethylene-based polymer may include polymerizing ethylene and at least one additional α-olefin in the presence of a catalyst system according to the present disclosure. The polymer resulting from such a catalyst system that incorporates the metal-ligand complex of formula (I) may have a density according to ASTM D792 (incorporated herein by reference in its entirety) from 0.850 $g/cm^3$ to 0.950 $g/cm^3$, from 0.880 $g/cm^3$ to 0.920 $g/cm^3$, from 0.880 $g/cm^3$ to 0.910 $g/cm^3$, or from 0.880 $g/cm^3$ to 0.900 $g/cm^3$, for example.

In another embodiment, the polymer resulting from the catalyst system according to the present disclosure has a melt flow ratio ($I_{10}/I_2$) from 5 to 15, where the melt index, $I_2$, is measured according to ASTM D1238 (incorporated herein by reference in its entirety) at 190° C. and 2.16 kg load and melt index $I_{10}$ is measured according to ASTM D1238 at 190° C. and 10 kg load. In other embodiments the melt flow ratio ($I_{10}/I_2$) is from 5 to 10, and in others, the melt flow ratio is from 5 to 9.

In some embodiments, the polymer resulting from the catalyst system according to the present disclosure has a molecular-weight distribution (MWD) from 1 to 25, where MWD is defined as $M_w/M_n$ with $M_w$ being a weight-average molecular weight and $M_n$ being a number-average molecular weight. In other embodiments, the polymers resulting from the catalyst system have a MWD from 1 to 6. Another embodiment includes a MWD from 1 to 3; and other embodiments include MWD from 1.5 to 2.5.

Embodiments of the catalyst systems described in this disclosure yield unique polymer properties as a result of the high molecular weights of the polymers formed and the amount of the co-monomers incorporated into the polymers.

Ethylene Polymerization Experiments

For the polymerization procedure in toluene, a 150-mL glass pressure vessel (dried in a 120° C. oven overnight prior to use) is loaded with 40 mL of dry toluene inside the glovebox. A large magnetic stir bar is added to the pressure vessel, and the pressure vessel is sealed, taken out of the glovebox, and attached to a high-pressure/high-vacuum line. The pressure vessel is cooled to −78° C. with a dry ice/acetone bath and degassed. Then, pressure vessel is warmed and equilibrated at the desired reaction temperature for 30 minutes using an external bath. The toluene is saturated with 1.0 atm of ethylene at the same time. The catalytically active species is generated by mixing measured amounts of procatalyst and co-catalyst in a vial in the glovebox (10 mL of toluene) and shaking for 10 min. The catalyst solution is removed from the glovebox and quickly injected into the rapidly stirring toluene solution using a gastight syringe equipped with a spraying needle. After the measured time interval, the reaction was quenched by introducing 5 mL of methanol. The reactor was vented to atmosphere and 10% HCl in methanol was added to the polymerization mixture to precipitate the polymer. The precipitated polymer was stirred for several hours, filtered, washed with methanol, and collected. It was then dried under high vacuum at 80° C. overnight until reaching a constant weight.

1-Octene Incorporation FIR Analysis

The running of samples for the HT-GPC analysis precedes the IR analysis. For the IR analysis, a 48-well HT silicon wafer is utilized for deposition and analysis of 1-octene incorporation of samples. For the analysis, the samples are heated to 160° C. for less than or equal to 210 minutes; the samples are reheated to remove magnetic GPC stir bars and are shaken with glass-rod stir bars on a J-KEM Scientific heated robotic shaker. Samples are deposited while being heated using a Tecan MiniPrep 75 deposition station, and the 1,2,4-trichlorobenzene is evaporated off the deposited wells of the wafer at 160° C. under nitrogen purge. The analysis of 1-octene is performed on the HT silicon wafer using a *NEXUS* 670 E.S.P. FT-IR.

HT-GPC Analysis

The molecular weight data is determined by analysis on a hybrid Symyx/Dow built Robot-Assisted Dilution High-Temperature Gel Permeation Chromatographer (Sym-RAD-GPC). The polymer samples are dissolved by heating for 120 minutes at 160° C. in 1,2,4-trichlorobenzene (TCB) at a concentration of 10 mg/mL stabilized by 300 parts per million (ppm) of butylated hydroxyl toluene (BHT). Each sample is diluted to 1 mg/mL immediately before the injection of a 250 μL aliquot of the sample. The GPC is equipped with two Polymer Labs PLgel 10 μm MIXED-B columns (300×10 mm) at a flow rate of 2.0 mL/minute at 160° C. Sample detection is performed using a PolyChar IR4 detector in concentration mode. A conventional calibration of narrow polystyrene (PS) standards is utilized with apparent units adjusted to homo-polyethylene (PE) using known Mark-Houwink coefficients for PS and PE in TCB at this temperature.

2 L Parr Reactor Polymerization Procedure

The batch reactor polymerizations are conducted in a 2 L Parr batch reactor. The reactor is heated by an electrical heating mantle, and is cooled by an internal serpentine cooling coil containing cooling water. Both the reactor and the heating/cooling system are controlled and monitored by a Camile™ TG process computer. The bottom of the reactor is fitted with a dump valve, which empties the reactor contents into a stainless-steel dump pot, which is prefilled with a catalyst kill solution (typically 5 mL of a Irgafos/Irganox/toluene mixture). The dump pot is vented to a 30 gal, blow-down tank, with both the pot and the tank purged with nitrogen. All solvents used for polymerization or catalyst makeup are run through solvent purification columns to remove any impurities that may affect polymerization. The 1-octene and IsoparE were passed through 2 columns, the first containing A2 alumina, the second containing Q5. The ethylene was passed through 2 columns, the first containing A204 alumina and 4Åmol sieves, the second containing Q5 reactant. The nitrogen gas, used for transfers, is passed through a single column containing A204 alumna, 4Åmol sieves and Q5.

The reactor is loaded first from the shot tank that may contain Isopar E solvent and/or 1-octene, depending on desired reactor load. The shot tank is filled to the load set points by use of a lab scale to which the shot tank is mounted. After liquid feed addition, the reactor is heated up to the polymerization temperature set point. Ethylene is added to the reactor when at reaction temperature to maintain reaction pressure set point. Ethylene addition amounts are monitored by a micro-motion flow meter.

The catalyst and activators were mixed with the appropriate amount of purified toluene to achieve a desired molarity solution. The catalyst and activators were handled in an inert glove box, drawn into a syringe and pressure transferred into the catalyst shot tank. This was followed by 3 rinses of toluene, 5 mL each. The run timer began immediately after catalyst addition from the shot take to the reactor. These polymerizations were run for 10 min., then the agitator was stopped and the bottom dump valve opened to empty reactor contents to the dump pot. The dump pot contents are poured into trays placed in a lab hood where the solvent is evaporated off overnight. The trays containing the remaining polymer are then transferred to a vacuum oven, where they are heated up to 140° C. under vacuum to remove any remaining solvent. After the trays cool to ambient temperature, the polymers are weighed for yield and submitted for polymer testing.

Solubility Test Procedure (SI Standard Procedure)

Solubility tests are performed at room temperature (22.5±2.5° C.). The chosen temperature is kept constant in all relevant parts of the equipment. A vial is charged with 30 mg of the co-catalyst (sample) and 1 mL of solvent. The suspension of co-catalyst and solvent is stirred for 30 minute at ambient temperature. The mixture is filtered via a syringe filter into a tared vial and the solution was weighed (X g of solution). The solvent is removed completely under high vacuum and the vial was weighed again (Y g of sample). The "$\rho_{solvent}$" is the density of the solvent in g/mL. The solubility of co-catalyst in solvent was measured in units of mg/mL. The solubility of cocatalyst in solvent was calculated as follows:

$$\text{Solubility} = 1000 * Y * \frac{\rho_{solvent}}{X - Y} \quad (1)$$

One or more features of the present disclosure are illustrated in view of the examples as follows:

EXAMPLES

Examples 1 to 3 are synthetic procedures for intermediates and for isolated co-catalysts.

All manipulations of air-sensitive materials were performed with rigorous exclusion of $O_2$ and moisture in oven-dried Schlenk-type glassware on a dual manifold Schlenk line, interfaced to a high-vacuum line ($10^{-6}$ Torr), or in a $N_2$-filled MBraun glove box with a high-capacity recirculator (less than 1 ppm $O_2$). Argon (Airgas, pre-purified grade) was purified by passage through a supported MnO oxygen-removal column and an activated Davison 4 Å molecular sieve column. Ethylene (Airgas) was purified by passage through an oxygen/moisture trap (Matheson, model MTRP-0042-XX). Hydrocarbon solvents (n-pentane, n-hexane, 1-hexene, methylcyclohexane, and toluene) were dried using activated alumina columns according to the method described by Grubbs (see Pangborn, A. B.; Giardello, M. A.; Grubbs, R. H.; Rosen, R. K.; Timmers, F. J., Safe and Convenient Procedure for Solvent Purification. *Organometallics* 19%, 15 (5), 1518-1520.) and were then vacuum-transferred from Na/K alloy. Benzene-$d_6$ and toluene-$d_8$ (Cambridge Isotope Laboratories, 99+ atom % D) were stored over Na/K alloy in vacuum and vacuum-transferred immediately prior to use. 1,2-Difluorobenzene and chlorobenzene-$d_5$ were dried with $CaH_2$ and distilled under vacuum. Chloroform-$d_3$ and 1,1,2,2-tetrachloroethane-$d_2$ were used as received (Cambridge Isotope Laboratories, 99+ atom % D).

SYNTHESIS OF COMPOUNDS

Example 1: Synthesis of n-Octyl Trityl Alcohol

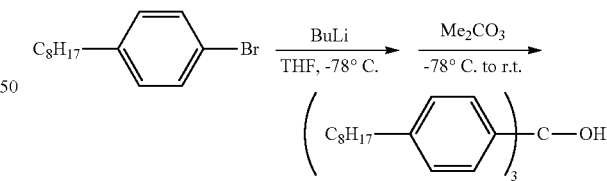

N-butyl lithium (11.5 mmol, 4.6 mL, 2.5 M in hexanes) was slowly added via syringe to a THF (50 mL) solution of p-octylbromobenzene (3.10 g, 11.5 mmol) at −78° C. The reaction was kept at −78° C. for 0.5 h. $Me_2CO_3$ (0.33 g, 3.64 mmol, 0.31 mL) was added to the solution via syringe. The solution was then warmed to room temperature. After the solution was stirred overnight, water was added to the solution to quench the reaction. The mixture was extracted three times with $Et_2O$, and the organic extracts were combined and washed twice with brine, dried ($Na_2SO_4$), filtered, and concentrated to dryness. The resulting crude product was purified by flash column chromatography using basic aluminum oxide (activated, basic, Brockmann I, from Aldrich). Gradient elution (hexanes, hexanes/EtOAc in a 50/1 ratio, EtOAc) gave the pure product as a colorless oil, 1.33 g, 58.1% yield.

$^1$H NMR (400 MHz, $C_2D_2Cl_4$) δ 7.36-7.10 (m, 12H), 2.71-2.57 (m, 6H), 1.67 (m, 6H), 1.44-1.25 (m, 30H), 1.02-0.85 (m, 9H). $^{13}$C NMR (151 MHz, $C_2D_2Cl_4$) δ 144.16, 141.63, 127.68, 127.63, 81.85 ($Ar_3C$, weak signal, confirmed by HMBC experiment), 35.42, 31.77, 31.28, 29.37, 29.32, 29.15, 22.60, 14.14. HR-MS (ESI) Calcd for $C_{43}H_{63}$ (M-OH)$^+$: 579.4930, Found: 579.4946.

Example 2: Synthesis of n-Octyl Trityl Chloride

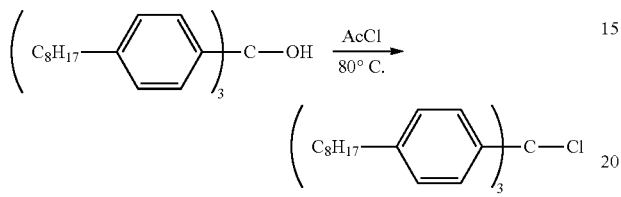

Acetyl chloride (0.265 g, 3.37 mmol, 0.24 mL) was added via syringe to a stirred solution of n-octyl trityl alcohol (0.67 g, 1.12 mmol) in toluene (20 mL) at 80° C. The reaction was kept at 80° C. for 1 h. All volatiles were removed, and the resulting oil product was further dried under high vacuum. The product light yellow oil was pure enough without further purification and a quantitative yield of 0.69 g.

$^1$H NMR (499 MHz, $CDCl_3$) δ 7.13 (m, 6H), 7.09 (m, 6H), 2.59 (m, 6H), 1.61 (m, 6H), 1.41-1.16 (m, 30H), 0.88 (m, 9H). $^{13}$C NMR (101 MHz, $CDCl_3$) δ 142.88, 142.41, 129.56, 127.58, 81.82 (Ar3C, weak signal, confirmed by HMBC experiment), 35.52, 31.89, 31.26, 29.47, 29.40, 29.25, 22.67, 14.10. HR-MS (ESI) Calculated for $C_{43}H_{63}$ (M-Cl)$^+$: 579.4930, Found: 579.4936.

Example 3: Synthesis of Inventive Co-Catalyst 1

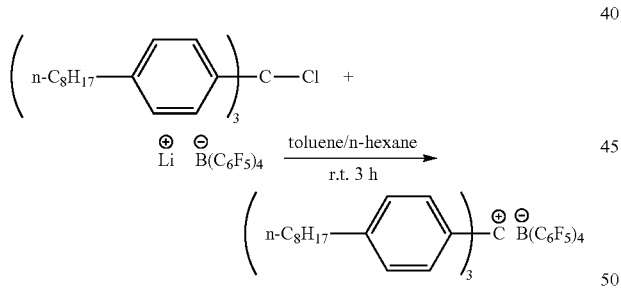

LiB($C_6F_5$)$_4$ was synthesized according to literature (Galland, G. B.; De Souza, R. F.; Mauler, R. S.; Nunes, F. F., *Macromolecules* 1999, 32, 1620-1625). LiB($C_6F_5$)$_4$ (0.13 g, 0.21 mmol) and n-octyl trityl chloride (0.21 g, 0.25 mmol) were mixed in a solution of 15 mL of toluene and 5 mL of n-hexane in the glovebox. After 3 hours, the solution was filtered through Celite. The solvent was removed under reduced pressure and the resulting oil was washed twice with 10 mL of cold pentane (−78° C.). After drying under high vacuum, the product was collected as a red oil, with 0.15 g, 58% yield.

$^1$H NMR (499 MHz, $CD_2Cl_2$) 7.67 (d, J=8.0 Hz, 6H), 7.55 (d, J=7.9 Hz, 6H), 2.94 (m, 6H), 1.79 (m, 6H), 1.49-1.27 (m, 30H), 0.91 (m, 9H). $^{19}$F NMR (470 MHz, $CD_2Cl_2$) 6-133.14 (m, m-F, 8F), −163.85 (t, p-F, 4F), −167.66 (m, o-F, 8F). Elem. Anal. Calcd for $C_{67}H_{63}BF_{20}$: C, 63.92, H, 5.04; Found: C, 64.13, H, 5.42

The structures of the co-catalysts that were investigated in the following examples are shown below:

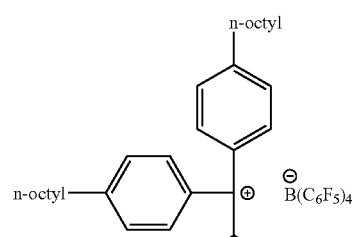

Inventive Co-catalyst 1

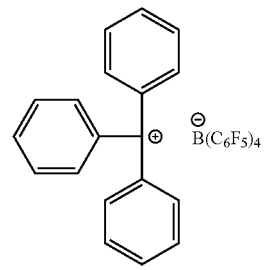

Comparative Co-catalyst C1

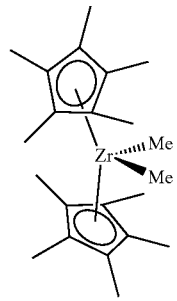

Catalyst Cp*$_2$ZrMe$_2$

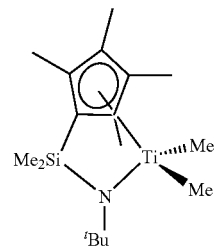

Catalyst Ti1

The Co-catalyst 1 has a structure including a non-coordinating borate anion [B($C_6F_5$)$_4$]$^{1-}$ and a cation according to formula (I) as previously described. Comparative Co-catalyst C1 did not have a cation according to formula (I). Solubility of Co-catalyst 1 and comparative Co-catalyst C1 were assessed as described by the solubility test procedure previously described. Solubility test results, as shown in Table 1, suggests alkyl substitution on the trityl group significantly increase solubility in methylcyclohexane (MCH). Comparative Co-catalyst C1 has negligible solubility in MCH while Co-catalyst 1 has good solubility (greater than 30 mg/mL MCH). Generally, polymerizations are carried out with about 10 mg of cocatalyst in 50 mL of solvent in lab. Thus, the solubility of Co-catalyst 1 is high enough for catalysis in aliphatic solvent such as MCH.

TABLE 1

Solubility of Alkyl-Substituted Trityl Co-catalysts*

| Co-catalyst | Solvent | Solubility |
| --- | --- | --- |
| Co-catalyst 1 | Toluene | >30 |
| Co-catalyst 1 | MCH | >30 |
| Co-catalyst C1 | MCH | 0 |

*In unit of mg of co-catalyst per mL of solvent.

Ethylene was polymerized in glass pressure vessel with a catalyst system including zirconium procatalyst and one of Co-catalyst 1 or Comparative Co-catalyst C1, as previously described. Catalyst activities of each system were measured, and the resulting polymers were characterized. Catalyst activity data and polymer characterization data are summarized in Table 2.

The polymerization conditions that provided the data in Table 2 were as follows: the 10 μmol of procatalyst $Zr_1$ and 10 μmol of Co-Catalyst 1 were mixed for 10 min before injecting into reactor to start reaction. The reactor contained 50 mL of solvent; ethylene was added at 1 atm; and the temperature of water bath was 25° C.

TABLE 2

Ethylene-based Polymerization Data[a]

| | Co-catalyst | Solvent | Time/min | Polymer (g) | Act.[b] | $M_n$[c] (kg/mol) | Đ[c] |
| --- | --- | --- | --- | --- | --- | --- | --- |
| 1 | Inventive 1 | PhCl | 3.5 | 1.51 | 2589 | 161 | 2.3 |
| 2 | Inventive 1 | Tol | 3.5 | 1.22 | 2091 | 107 | 2.5 |
| 3 | Inventive 1 | MCH | 3.5 | 1.52 | 2606 | 126 | 2.2 |
| 4 | Comparative C1 | MCH | 3.5 | 0 | Cocatalyst insoluble | | |

[a]Conditions: procatalyst, $Cp*_2ZrMe_2$, 10 μmol; co-catalyst, 10 μmol; ethylene, 1 atm; temperature of water bath, 25° C.; solvent, 50 mL;
[b]Unit is kg · (mol of metal)$^{-1}$ · h$^{-1}$ · atm$^{-1}$.
[c]Determined by GPC against polystyrene standards in (g · mol$^{-1}$).

As shown by the data recorded in Table 2, a change in the solvent influences catalytic activity. In chlorobenzene (PhCl), the activity of the polymerization system is 2589 kg·(mol of metal)$^{-1}$ h$^{-1}$·atm$^{-1}$. In MCH, the activity of the polymerization system including Inventive 1 was greater than that of the same system in toluene and similar to the system in PhCl, namely 2606 kg·(mol of metal)$^{-1}$·h$^{-1}$·atm$^{-1}$. In contrast, polymerization reactions that included Comparative $C_1$ as the co-catalyst in MCH showed no activity. It is believed that the inactivity of the system may have resulted from the insolubility of Comparative Co-catalyst C1 in MCH. Based on the success of the hydrocarbon solvent, it is expected that the inventive systems can perform well in other hydrocarbon systems.

The result summarized in Table 3 shows an example of olefin polymerization with a titanium catalyst and Inventive Co-catalyst 1 under higher temperature and pressure (100° C. and 150 psig). Under these conditions the Inventive Co-catalyst 1 was part of an active catalyst package in the hydrocarbon solvent Isopar E for ethylene/1-octene copolymerization.

Equipment Standards

All solvents and reagents are obtained from commercial sources and used as received unless otherwise noted. Anhydrous toluene, hexanes, tetrahydrofuran, and diethyl ether are purified via passage through activated alumina and, in some cases, Q-5 reactant. Solvents used for experiments performed in a nitrogen-filled glovebox are further dried by storage over activated 4 Å molecular sieves. Glassware for moisture-sensitive reactions is dried in an oven overnight prior to use. NMR spectra are recorded on Varian 400-MR and VNMRS-500 spectrometers. LC-MS analyses are performed using a Waters e2695 Separations Module coupled with a Waters 2424 ELS detector, a Waters 2998 PDA detector, and a Waters 3100 ESI mass detector. LC-MS separations are performed on an XBridge C18 3.5 μm 2.1×50 mm column using a 5:95 to 100:0 acetonitrile to water gradient with 0.1% formic acid as the ionizing agent. HRMS analyses are performed using an Agilent 1290 Infinity LC with a Zorbax Eclipse Plus C18 1.8 μm 2.1×50 mm column coupled with an Agilent 6230 TOF Mass Spectrometer with electrospray ionization. $^1$H NMR data are reported as follows: chemical shift (multiplicity (br=broad, s=singlet, d=doublet, t=triplet, q=quartet, p=pentet, sex=sextet, sept=septet and m=multiplet), integration, and assignment). Chemical shifts for $^1$H NMR data are reported in ppm downfield from internal tetramethylsilane (TMS, δ scale) using residual protons in the deuterated solvent as references. $^{13}$C NMR data are determined with $^1$H decoupling, and the chemical shifts are reported downfield from tetramethylsilane (TMS, δ scale) in ppm versus the using residual carbons in the deuterated solvent as references.

TABLE 3

Ethylene/1-octene copolymerization with catalyst A and Co-catalyst B at 100° C. in a 2 L Parr reactor

| Entry | Catalyst | Catalyst loading (μmol) | Co-catalyst | Activator Loading (μmol) | Yield (g) | Mw (g/mol) | PDI | 1-Octene incorporation (mol %) |
| --- | --- | --- | --- | --- | --- | --- | --- | --- |
| 1 | Ti1 | 0.3 | Inventive 1 | 0.36 | 67.0 | 51,000 | 2.2 | 28.8 |

Conditions: 100° C., 150 psig, 750 g Isopar E, 160 g 1-octene in a 2 L Parr reactor, 10 minute reaction time, 1-octene incorporation measured by FTIR, Mw and PDI measured by HT-GPC

The invention claimed is:

1. A catalyst system comprising:
   a procatalyst; and
   a co-catalyst comprising:
      a non-coordinating borate anion having the formula $[B(C_6F_5)_4]^{1-}$ and a cation according to formula (I):

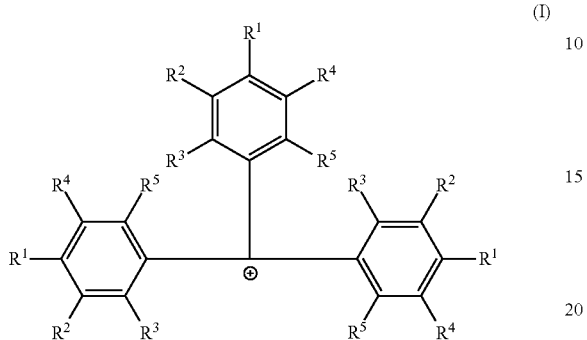

(I)

where:
   each $R^1$, $R^2$, $R^3$, $R^4$, and $R^5$ is independently chosen from —H, —F, —Cl, substituted or unsubstituted $(C_4-C_{40})$alkyl, substituted or unsubstituted $(C_4-C_{40})$alkenyl or substituted or unsubstituted $(C_4-C_{40})$cycloalkyl, wherein the substituted $(C_4-C_{40})$alkyl and substituted $(C_4-C_{40})$cycloalkyl are substituted with one or more $R^S$, where each $R^S$ is chosen from $(C_1-C_{20})$alkyl or halogen;
   provided that at least one of $R^1$, $R^2$, $R^3$, $R^4$, or $R^5$ is chosen from substituted or unsubstituted $(C_4-C_{40})$alkyl or substituted or unsubstituted $(C_4-C_{40})$cycloalkyl.

2. The catalyst system according to claim 1, wherein the co-catalyst is dissolved in a non-halogenated solvent.

3. The catalyst system according to claim 1, wherein the catalyst is ionic.

4. The catalyst system according to claim 1, wherein each $R^1$ is independently $(C_4-C_{30})$alkyl.

5. The catalyst system according to claim 1, wherein each $R^1$ is independently chosen from n-butyl, tert-butyl, 1-pentyl, 1-hexyl, heptyl, n-octyl, nonyl, decyl, undecyl, or dodecyl.

6. The catalyst system according to claim 1, wherein each $R^1$ is independently tert-butyl, tert-octyl, or n-octyl.

7. The catalyst system according to claim 1, wherein each of $R^2$, $R^3$, $R^4$ and $R^5$ are —H.

8. The catalyst system according claim 1, wherein each $R^1$, $R^2$, $R^3$, $R^4$, or $R^5$ is $[C_{40}]$alkyl optionally substituted with one or more $R^S$, and where each $R^S$ is chosen from $(C_1-C_{20})$alkyl or halogen.

9. The catalyst system according to claim 1, wherein the co-catalyst has a solubility of greater than 20 milligrams per milliliter (mg/mL) in toluene under standard temperature and pressure.

10. A polymerization process for producing ethylene-based polymer, the process comprising:
    polymerizing ethylene and optionally one or more α-olefins in the presence of a catalyst system, the catalyst system comprising a catalyst and a co-catalyst dissolved in a non-halogenated hydrocarbon solvent, wherein the co-catalyst comprises:
       a non-coordinating borate anion having the formula $[B(C_6F_5)_4]^{1-}$
       a cation according to formula (I):

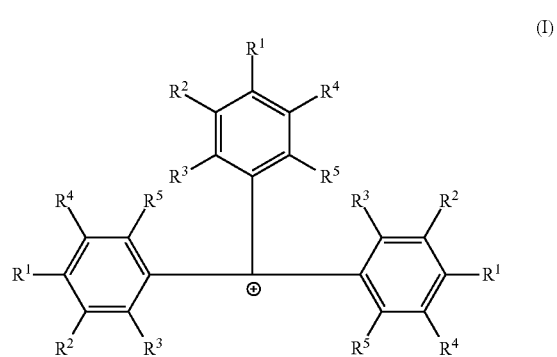

(I)

where:
   each $R^1$, $R^2$, $R^3$, $R^4$, and $R^5$ is independently chosen from —H, —F, —Cl, substituted or unsubstituted $(C_4-C_{40})$alkyl, substituted or unsubstituted $(C_4-C_{40})$alkenyl or substituted or unsubstituted $(C_4-C_{40})$cycloalkyl, wherein the substituted $(C_4-C_{40})$ alkyl and substituted $(C_4-C_{40})$cycloalkyl are substituted with one or more $R^S$, where each $R^S$ is chosen from $(C_1-C_{20})$alkyl or halogen;
   provided that at least one of $R^1$, $R^2$, $R^3$, $R^4$, or $R^5$ is chosen from substituted or unsubstituted $(C_4-C_{40})$ alkyl or substituted or unsubstituted $(C_4-C_{40})$cycloalkyl.

11. The process according to claim 10, wherein the α-olefin is 1-octene.

12. The process according to claim 10, wherein the non-halogenated hydrocarbon solvent is toluene or methylcyclohexane.

13. The process according to claim 10, wherein each $R^1$ is independently $(C_4-C_{30})$alkyl.

14. The process according to claim 10, wherein each of $R^2$, $R^3$, $R^4$ and $R^5$ are —H.

15. The process according to claim 10, wherein each $R^1$ is independently tert-butyl, tert-octyl, or n-octyl.

* * * * *